United States Patent
Appakutty (10) Patent No.: US 10,275,918 B2
(45) Date of Patent: Apr. 30, 2019

(54) METHOD AND SYSTEM FOR DETECTING VIRTUAL REALITY SICKNESS CAUSING CONTENT IN VIRTUAL REALITY MOTION SIMULATORS

(71) Applicant: Wipro Limited, Bangalore (IN)

(72) Inventor: Rajagopal Appakutty, Chennai (IN)

(73) Assignee: Wipro Limited, Bangalore (IN)

( * ) Notice: Subject to any disclaimer, the term of this patent is extended or adjusted under 35 U.S.C. 154(b) by 0 days.

(21) Appl. No.: 15/711,420

(22) Filed: Sep. 21, 2017

(65) Prior Publication Data

US 2019/0043232 A1    Feb. 7, 2019

(30) Foreign Application Priority Data

Aug. 2, 2017  (IN) .............. 201741027514

(51) Int. Cl.
*G06T 11/60*  (2006.01)
*G01P 15/14*  (2013.01)

(52) U.S. Cl.
CPC .............. *G06T 11/60* (2013.01); *G01P 15/14* (2013.01)

(58) Field of Classification Search
CPC ............................................. H04N 2213/002
USPC ....................................................... 345/633
See application file for complete search history.

(56) References Cited

U.S. PATENT DOCUMENTS

| 6,361,508 | B1 | 3/2002 | Johnson et al. |
| 7,469,162 | B2 | 12/2008 | Lattner et al. |
| 8,708,884 | B1 | 4/2014 | Smyth |
| 2012/0134543 | A1* | 5/2012 | Fedorovskaya .... H04N 13/0033 382/107 |
| 2017/0075417 | A1* | 3/2017 | Asami ..................... A63F 13/25 |

FOREIGN PATENT DOCUMENTS

WO    02056792 A2    7/2002

* cited by examiner

*Primary Examiner* — Thomas J Lett
(74) *Attorney, Agent, or Firm* — Pepper Hamilton LLP (57) ABSTRACT

The present disclosure relates to methods, non-transitory computer readable media, and devices, for detecting virtual reality sickness causing content in virtual reality motion simulators. A visual perception measurement of a virtual reality content being displayed on a head-mounted virtual reality device of a virtual reality motion simulator is determined. A vestibular perception measurement of the virtual reality content is then determined. The visual perception measurement and the vestibular perception measurement of the virtual reality content are compared. An indication of a user experience in the virtual reality motion simulator is determined based on the comparison and the indication of the user experience is output.

18 Claims, 5 Drawing Sheets

METHOD AND SYSTEM FOR DETECTING VIRTUAL REALITY SICKNESS CAUSING CONTENT IN VIRTUAL REALITY MOTION SIMULATORS

This application claims the benefit of Indian Patent Application Serial No. 201741027514 filed Aug. 2, 2017, which is hereby incorporated by reference in its entirety.

FIELD

The present subject matter generally relates to field of virtual reality. More particularly, the present disclosure discloses a method and system for detecting virtual reality sickness causing content in virtual reality motion simulators.

BACKGROUND

The present subject matter generally relates to field of virtual reality. More particularly, the present disclosure discloses a method and system for detecting virtual reality sickness causing content in virtual reality motion simulators.

SUMMARY

Embodiments of present disclosure disclose a method of detecting virtual reality sickness causing content in virtual reality motion simulators. The method includes determining, by a virtual reality system, a visual perception measurement of a virtual reality content being displayed to a user on a head mounted virtual reality device of a virtual reality motion simulator. The method also includes determining, by the virtual reality system, a vestibular perception measurement of the virtual reality content being sensed by the user mounted on a platform of the virtual reality motion simulator and wearing the head mounted virtual reality device. The method further includes comparing the visual perception measurement and the vestibular perception measurement of the virtual reality content experienced by the user. Further, the method includes identifying user experience of the user in the virtual reality motion simulator.

Disclosed herein is a virtual reality system for detecting virtual reality sickness causing content in virtual reality motion simulators. The virtual reality system includes a virtual reality motion simulator, a processor and a memory. The virtual reality motion simulator includes a head mounted virtual reality device and a platform. The head mounted virtual reality device is configured to be accommodated on a head of a user and display a virtual reality content to the user. The head mounted virtual reality device further includes at least one head mounted inertial measurement unit (IMU) sensor. The platform is configured to accommodate the user and physically orient in accordance with the virtual reality content. The platform further includes a platform IMU sensor. The memory is communicatively coupled to the processor, where the memory stores processor-executable instructions, which, on execution, cause the processor to determine a visual perception measurement of a virtual reality content being displayed to the user on the head mounted virtual reality device of the virtual reality motion simulator; determine a vestibular perception measurement of the virtual reality content being sensed by the user mounted on the platform of the virtual reality motion simulator and wearing the head mounted virtual reality device; compare the visual perception measurement and the vestibular perception measurement of the virtual reality content experienced by the user; and identify user experience of the user in the virtual reality motion simulator.

Further, the present disclosure comprises a non-transitory computer readable medium including instructions stored thereon that when processed by at least one processor causes a virtual reality system to perform operations comprising determining a visual perception measurement of a virtual reality content being displayed to a user on a head mounted virtual reality device of a virtual reality motion simulator. Further, the instructions cause the processor to determine a vestibular perception measurement of the virtual reality content being sensed by the user mounted on a platform of the virtual reality motion simulator and wearing the head mounted virtual reality device. Further, the instructions cause the processor to compare the visual perception measurement and the vestibular perception measurement of the virtual reality content experienced by the user. Furthermore, the instructions cause the processor to identify user experience of the user in the virtual reality motion simulator.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE DRAWINGS

The accompanying drawings, which are incorporated in and constitute a part of this disclosure, illustrate exemplary embodiments and, together with the description, serve to explain the disclosed principles. In the figures, the left-most digit(s) of a reference number identifies the figure in which the reference number first appears. The same numbers are used throughout the figures to reference like features and components. Some embodiments of system and/or methods in accordance with embodiments of the present subject matter are now described, by way of example only, and with reference to the accompanying figures, in which.

It should be appreciated by those skilled in the art that any block diagrams herein represent conceptual views of illustrative systems embodying the principles of the present subject matter. Similarly, it will be appreciated that any flow charts, flow diagrams, state transition diagrams, pseudo code, and the like represent various processes which may be substantially represented in computer readable medium and executed by a computer or processor, whether or not such computer or processor is explicitly shown.

DETAILED DESCRIPTION

In the present document, the word "exemplary" is used herein to mean "serving as an example, instance, or illustration." Any embodiment or implementation of the present subject matter described herein as "exemplary" is not necessarily to be construed as preferred or advantageous over other embodiments.

While the disclosure is susceptible to various modifications and alternative forms, specific embodiment thereof has been shown by way of example in the drawings and will be described in detail below. It should be understood, however, that it is not intended to limit the disclosure to the particular forms disclosed, but on the contrary, the disclosure is to cover all modifications, equivalents, and alternative falling within the scope of the disclosure.

The terms "comprises", "comprising", or any other variations thereof, are intended to cover a non-exclusive inclusion, such that a setup, device or method that comprises a list of components or steps does not include only those components or steps but may include other components or steps not expressly listed or inherent to such setup or device or method. In other words, one or more elements in a system or apparatus proceeded by "comprises . . . a" does not, without more constraints, preclude the existence of other elements or additional elements in the system or apparatus.

In the following detailed description of the embodiments of the disclosure, reference is made to the accompanying drawings that form a part hereof, and in which are shown by way of illustration specific embodiments in which the disclosure may be practiced. These embodiments are described in sufficient detail to enable those skilled in the art to practice the disclosure, and it is to be understood that other embodiments may be utilized and that changes may be made without departing from the scope of the present disclosure. The following description is, therefore, not to be taken in a limiting sense.

Figure 1A:
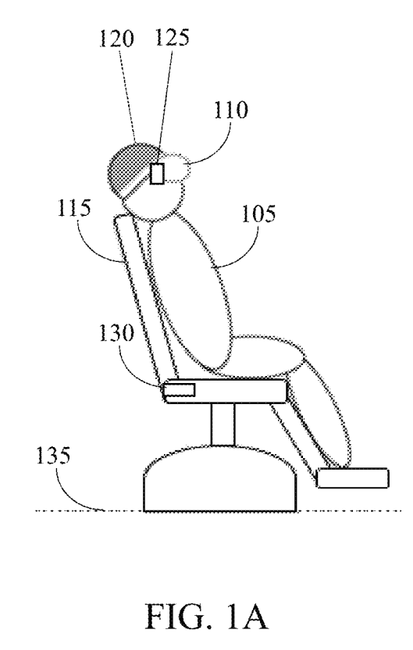
FIG. 1A and FIG. 1B illustrate a side view of a user in a virtual reality motion simulator environment, in accordance with some embodiments of the present disclosure.
Figure 1B:
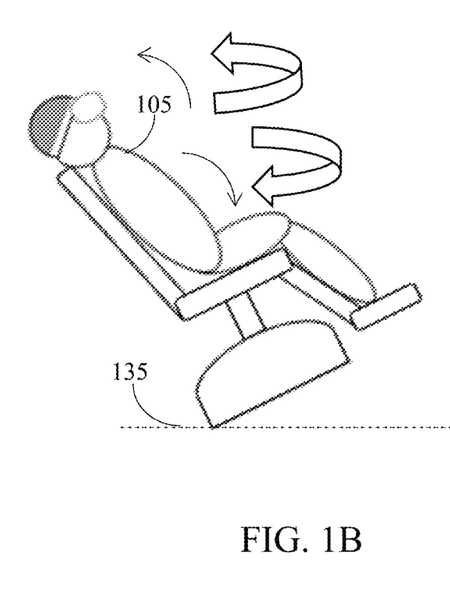

FIG. 1A and FIG. 1B illustrate a side view of a user in a virtual reality motion simulator environment 100, in accordance with some embodiments of the present disclosure.

The virtual reality motion simulator environment 100 includes a user 105 using a virtual reality motion simulator in a virtual reality system. The virtual reality motion simulator includes a head mounted virtual reality device 110 and a platform 115. The head mounted virtual reality device 110 is accommodated on head of the user 105 and covers eyes of the user 105. The head mounted virtual reality device 110 includes at least one head mounted inertial measurement unit (IMU) sensor, for example a head mounted IMU sensor 120 and a head mounted IMU sensor 125. The head mounted IMU sensor 120 is coupled to the head mounted virtual reality device 110 above left ear of the user 105 and the head mounted IMU sensor 125 is coupled to the head mounted virtual reality device 110 above right ear of the user 105. The user 105 is mounted on the platform 115. Examples of the platform 115 include, but are not limited to, a motorized gaming chair, a boat shaped simulator, and the like. The platform 115 includes a platform IMU sensor 130. In some embodiments, each of the head mounted IMU sensor 120, the head mounted IMU sensor 125, and the platform IMU sensor 130 includes a gyrometer sensor and an orientation sensor.

As illustrated in FIG. 1A, the user 105 is mounted on the platform 115, for example the motorized gaming chair, and is wearing the head mounted virtual reality device 110. In some embodiments, the virtual reality motion simulator is coupled to a computer system (not shown in FIG. 1A) in the virtual reality motion simulator environment 100 that provides a virtual reality application for displaying virtual reality content to the user 105 through the head mounted virtual reality device 110. In other embodiments, an electronic device (not shown in FIG. 1A), for example a mobile phone, may be accommodated in the head mounted virtual reality device 110 to display the virtual reality content to the user 105. The platform 115 is configured to physically orient in accordance with the virtual reality content that is being displayed on the head mounted virtual reality device 110. For instance, the user 105 is mounted on the platform 115 in an upright position relative to a floor 135, in FIG. 1A. In another instance, the user 105 mounted on the platform 115 is physically oriented in different directions relative to the floor 135 in accordance with the virtual reality content, as illustrated in FIG. 1B.

In one example, the user 105 is wearing the head mounted virtual reality device 110 and mounted on the platform 115, for example a motorized gaming chair, which matches movements the user 105 makes in a game. In another example, the user 105 experiences a virtual reality roller coaster ride where the motorized gaming chair rotates in three axes. In another example, the user 105 can experience a virtual reality boat ride where the motorized gaming chair sways physically giving users a feeling of being in a boat.

The computer system or the electronic device is configured to determine a visual perception measurement of a virtual reality content being displayed to the user 105 on the head mounted virtual reality device 110 of the virtual reality motion simulator. A vestibular perception measurement of the virtual reality content being sensed by the user 105 mounted on the platform 115 of the virtual reality motion simulator and wearing the head mounted virtual reality device 110 is further determined. The vestibular perception measurement is determined by simulating a vestibular system present in inner ears of the user 105 to measure physical orientation of the user 105. The computer system or the electronic device is configured to further compare the visual perception measurement and the vestibular perception measurement of the virtual reality content experienced by the user 105, and identify user experience of the user 105 in the virtual reality motion simulator. The computer system or the electronic device is described in detail with reference to FIG. 5.

In some embodiments, operation of the virtual reality system for detecting the virtual reality sickness causing content during usage of the virtual reality motion simulator is explained in detail with reference to FIG. 2.

Figure 2:
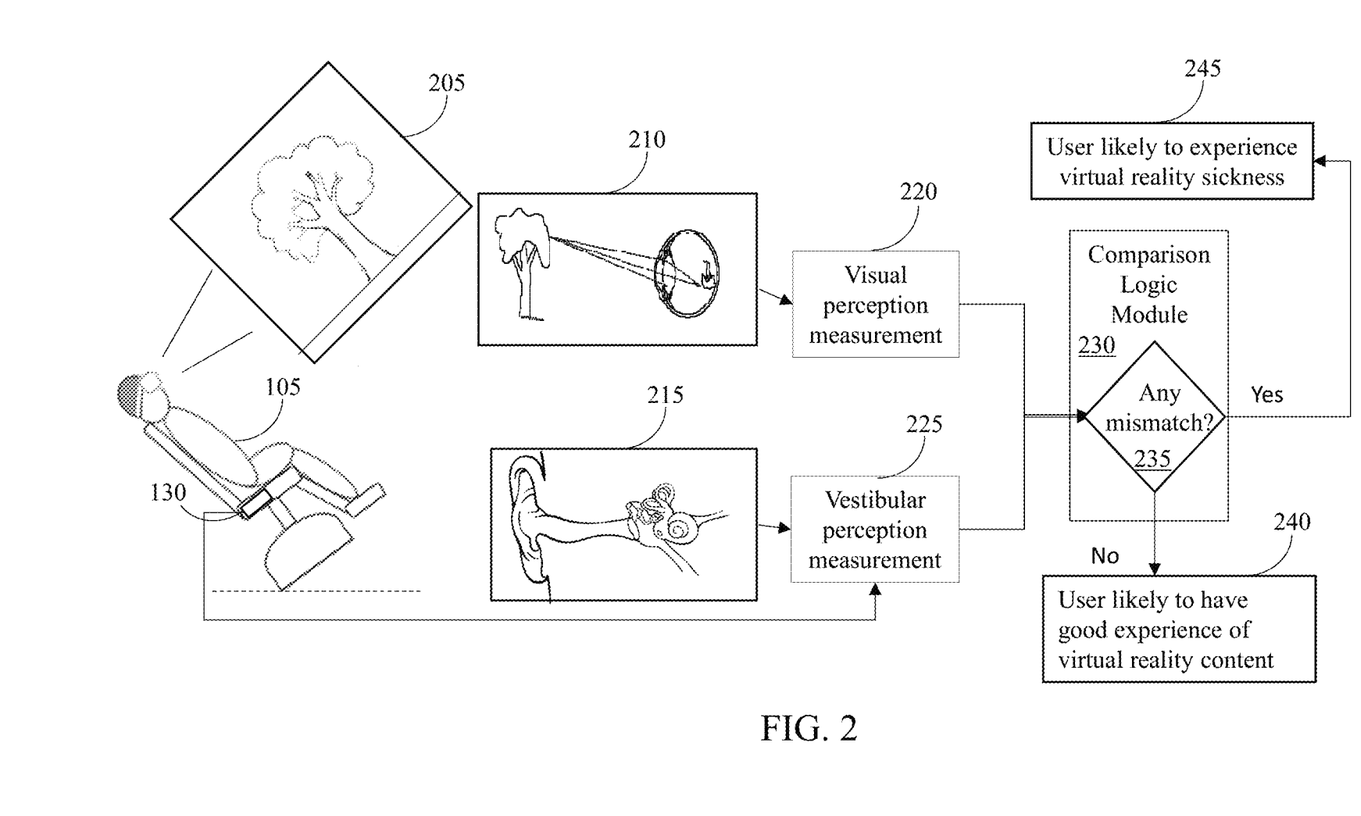
FIG. 2 is a flow diagram illustrating a method of detecting virtual reality sickness causing content during usage of a virtual reality motion simulator, in accordance with some embodiments of the present disclosure.

Referring now to FIG. 2, a flow diagram of a method of detecting the virtual reality sickness causing content during usage of the virtual reality motion simulator is illustrated, in accordance with some embodiments of the present disclosure. The user 105 is seated on the platform 115 and wearing the head mounted virtual reality device 110. The platform 115 is physically oriented in accordance with a virtual reality content 205 being displayed to the user.

A visual data 210 is captured by eyes of the user 105. A vestibular data 215 is captured by inner ears of the user 105 as well as from the platform IMU sensor 130. The visual data 210 is used to determine visual perception measurement 220 and the vestibular data 215 is used to determine vestibular perception measurement 225. The visual perception measurement 220 of the virtual reality content 205 is determined by determining a visual orientation angle of the virtual reality content 205 based on a relative angle of a virtual floor with respect to a virtual camera.

In some embodiments, the visual perception measurement 220 or visually perceived orientation of the floors, landscape, trees, or mountains in the virtual reality content 205 is extracted by instrumenting a source code to sense the visual orientation angle of the virtual camera.

The vestibular perception measurement 225 of the virtual reality content 205 is determined as explained in detail with reference to FIG. 3.

A comparison logic module 230 in the computer system or the electronic device compares the visual perception measurement 220 and the vestibular perception measurement 225 of the virtual reality content 205 experienced by the user 105. A determination for any mismatch between the visual perception measurement 220 and the vestibular perception measurement 225 is performed at step 235. If there is no mismatch, the virtual reality content and in turn the virtual reality application is certified as safe content and the user 105 is likely to have a good experience of the virtual reality content 205, at step 240. If there is a mismatch, the virtual reality content 205 is certified as the virtual reality sickness causing content and the user 105 is likely to experience virtual reality sickness. In an example of the mismatch, the head mounted virtual reality device 110 may display a landscape (in the virtual reality content 205) at a 30 degree angle, while the physical orientation of the user 105 is at a 10-degree angle based on tilt of the platform 115. In some embodiments, the computer system or the electronic device can provide at least one correction method to correct the mismatch between the visual perception measurement 220 and the vestibular perception measurement 225 of the virtual reality content 205.

The determination of the vestibular perception measurement 225 is explained in detail with reference to FIG. 3.

Figure 3:
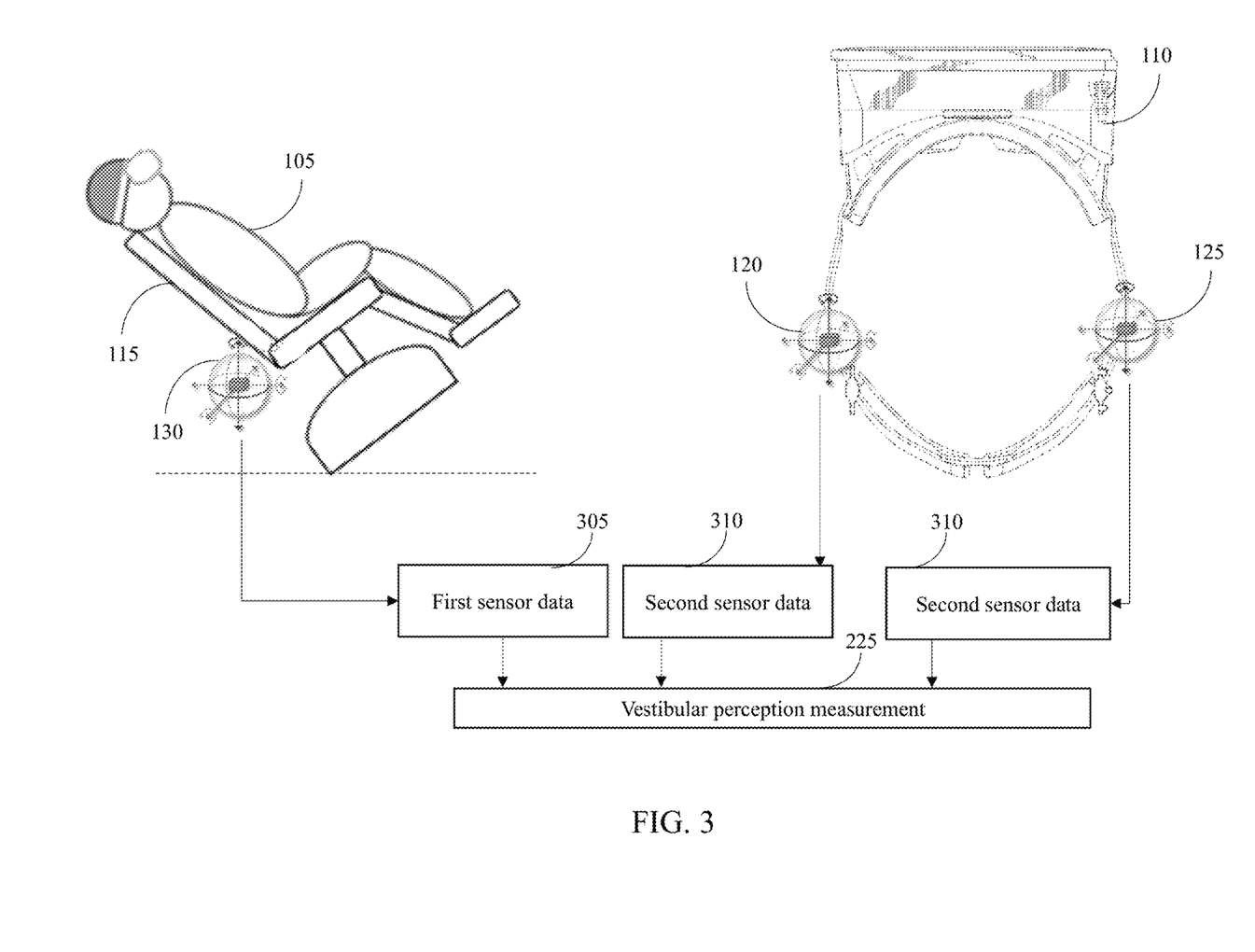
FIG. 3 is an exemplary illustration of determination of vestibular perception measurement, in accordance with some embodiments of the present disclosure.

FIG. 3 is an exemplary illustration of determination of the vestibular perception measurement 225, in accordance with some embodiments of the present disclosure. In the illustrated FIG. 3, the user 105 is mounted on the platform 115 which is physically oriented in accordance with the virtual reality content 205.

The platform IMU sensor 130 on the platform 115 senses first sensor data 305. The first sensor data includes data associated with physical orientation of the platform 115. The head mounted IMU sensor 120 senses second sensor data 310 of the left ear of the user 105 and the head mounted IMU sensor 125 senses the second sensor data 310 of the right ear of the user 105. The second sensor data 310 includes data associated with physical orientation of the head of the user 105 and which is sensed by the vestibular system of the user 105. The computer system or the electronic device combines the first sensor data 305 and the second sensor data 310 to derive orientation values. In some embodiments, the first sensor data 305 and the second sensor data 310 is combined or fused using a data fusion method to derive the orientation values. A vestibular perception angle is further determined based on the orientation values to determine the vestibular perception measurement 225.

Figure 4:
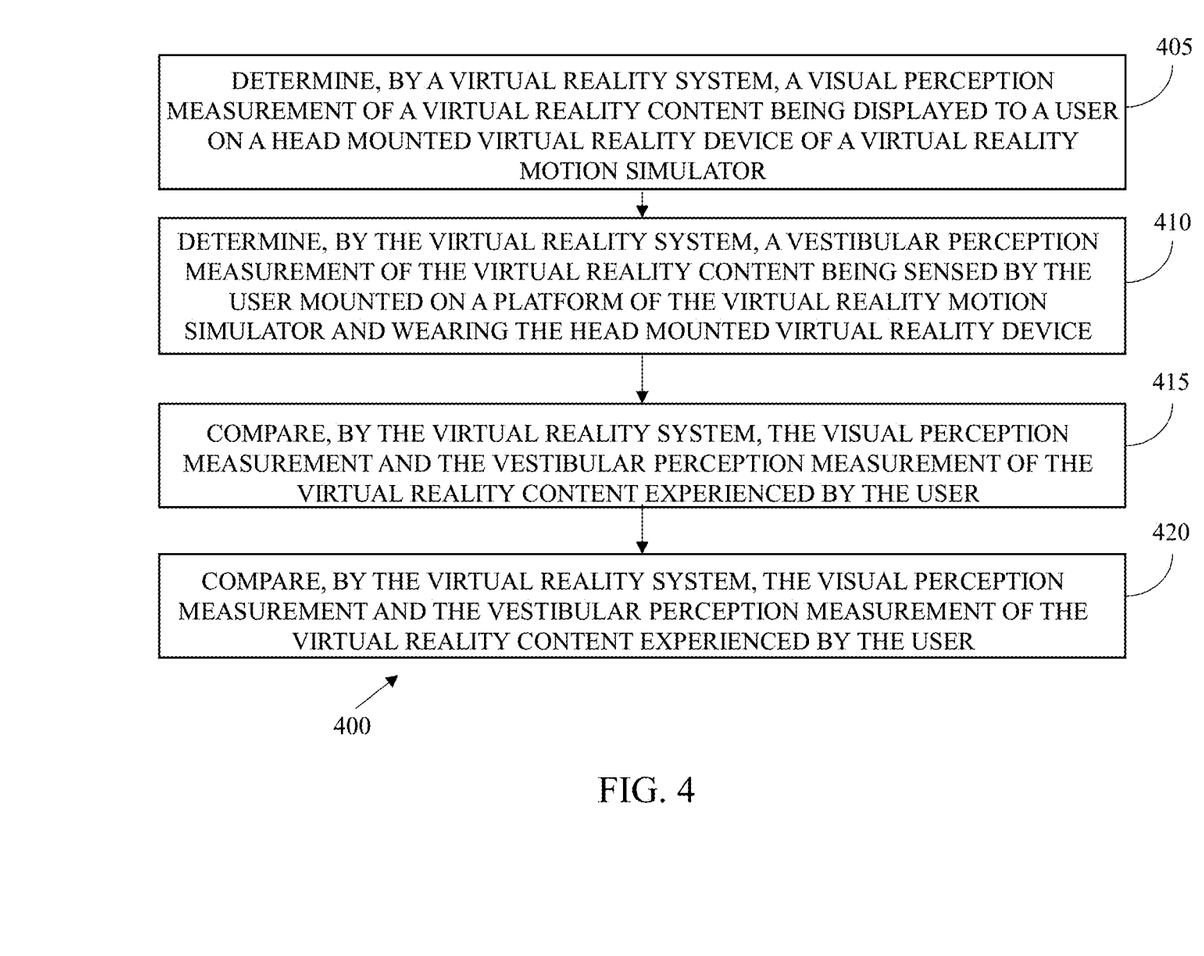
FIG. 4 is a flow diagram illustrating a method of detecting virtual reality sickness causing content during usage of a virtual reality motion simulator, in accordance with some embodiments of the present disclosure.

FIG. 4 is a flow diagram illustrating a method 400 of detecting virtual reality sickness causing content in virtual reality motion simulators, in accordance with some embodiments of the present disclosure. A virtual reality motion simulator includes a head mounted virtual reality device, for example a head mounted virtual reality device 110 of FIG. 1, and a platform, for example a platform 115 of FIG. 1. A user, for example the user 105 of FIG. 1, is mounted on the platform and is wearing the head mounted virtual reality device. The user is able to view virtual reality content displayed on the head mounted virtual reality device and be physically oriented along with the platform in accordance with the virtual reality content. In some embodiments, the virtual reality content is enabled to be displayed by a virtual reality application on a computer system or an electronic device. The virtual reality application delivers user experience by using a combination of the head mounted virtual reality device and the platform.

An example of the user experience includes a virtual reality based boat ride, where the user sitting on a motorized virtual reality chair experiences swaying of a boat as waves hit the boat. The virtual reality application programmatically controls physical tilting of the motorized virtual reality chair, and the virtual reality application displays a lake and water waves using the head mounted virtual reality device.

The order in which the method is described is not intended to be construed as a limitation, and any number of the described method blocks can be combined in any order to implement the method. Additionally, individual blocks may be deleted from the method without departing from the scope of the subject matter described herein.

At step 405, the method 400 includes determining, by a virtual reality system, a visual perception measurement of the virtual reality content being displayed to the user on the head mounted virtual reality device of the virtual reality motion simulator. In some embodiments, the visual perception measurement is determined by directly instrumenting a scripting logic so as to measure a relative angle of a virtual floor with respect to a virtual camera that simulates view of the user. The method of determining the visual perception measurement is explained with reference to FIG. 2 and is not explained herein for sake of brevity.

The visual perception measurement is determined by determining a visual orientation angle of the virtual reality content based on the relative angle of the virtual floor with respect to the virtual camera.

At step 410, the method 400 includes determining, by the virtual reality system, a vestibular perception measurement of the virtual reality content being sensed by the user mounted on the platform of the virtual reality motion simulator and wearing the head mounted virtual reality device.

In some embodiments, the vestibular perception measurement is determined by first measuring first sensor data from a platform inertial measurement unit (IMU) sensor attached to the platform. The first sensor data includes data associated with physical orientation of the platform. A second sensor data is subsequently measured from at least one head mounted IMU sensor attached to the head mounted virtual reality device. The second sensor data includes data associated with physical orientation of head of the user. The first sensor data and the second sensor data are combined to derive orientation values and a vestibular perception angle is determined based on the orientation values.

Figure 5:
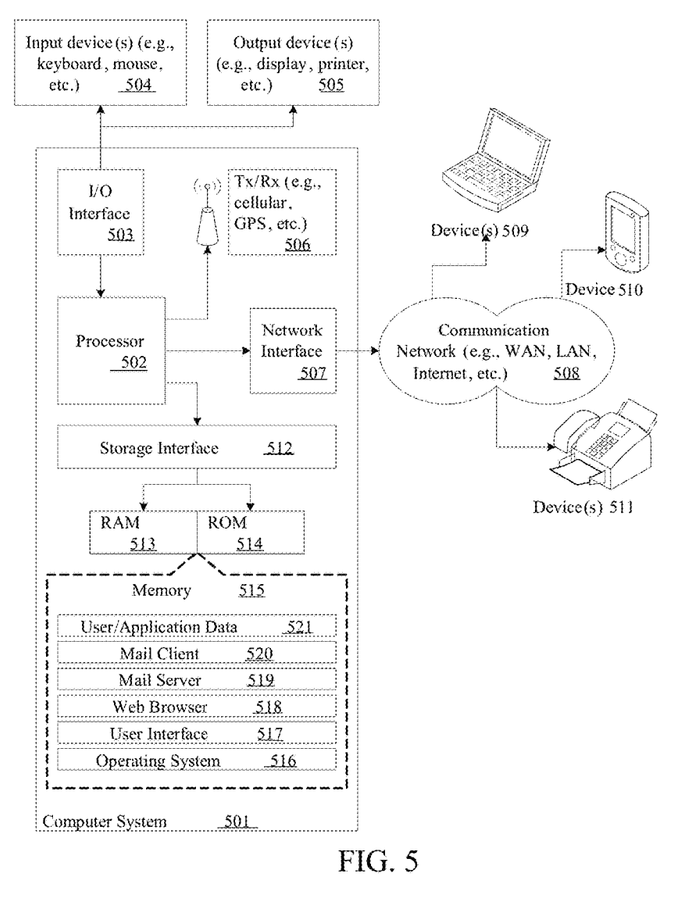
FIG. 5 illustrates a block diagram of an exemplary computer system for implementing various embodiments, in accordance with some embodiments of the present disclosure.

At step 415, the method 400 includes comparing, by the virtual reality system, the visual perception measurement and the vestibular perception measurement of the virtual reality content experienced by the user. A computer system or an electronic device as explained with reference to FIG. 5 is used to compare the visual perception measurement and the vestibular perception measurement using a comparison logic module, for example the comparison logic module 230 of FIG. 2. The visual perception measurement and the vestibular perception measurement is compared and the virtual reality content is certified as the virtual reality sickness causing content based on a mismatch between the visual perception measurement and the vestibular perception measurement of the virtual reality content. For instance, users of the virtual reality boat ride may experience virtual reality sickness or disorientation if visual scenes seen through the head mounted virtual reality device show the boat being tilted by a 45-degree angle due to a strong wave, but the motorized virtual reality chair only tilts by 10 degrees. If there is a match between the visual perception measurement and the vestibular perception measurement of the virtual reality content, the virtual reality content is certified as safe content.

In some embodiments, the method includes providing at least one correction method to correct the mismatch between the visual perception measurement and the vestibular perception measurement of the virtual reality content.

In some embodiments, the method includes detecting a level of the mismatch in orientation in each section of the virtual reality content. A decision that a virtual reality application is certified to not cause disorientation in the user is further reached, if the level of the mismatch is below a minimum acceptable threshold.

In one example, at a given instant of time, a motorized gaming chair may be at 30 degree angle in physical orientation. Assuming the user is seated on the VR chair and is looking steady, the head mounted IMU sensor placed near ears of the user will detect 30 degree angle, which will be same as a human brain will sense from biological vestibular system. In contrast if visual scenes of the virtual reality content shows the floor or landscape at 40 degree angle with respect to eyes of the user, both the values will be compared and the level of mismatch is measured as 40 degree angle subtracted by 30 degree angle. The mismatch in orientation between what is seen and what is experienced will be 10 degree angle. While a 10 degree angle mismatch may be within a minimal acceptable threshold, a large value of the mismatch, especially if lasts for a long duration, can certify that the particular virtual reality application can cause virtual reality sickness in the user. However, if the visual scenes shows the floor or landscape at 30 degree angle with respect to the eyes of the user, both the values are compared and the level of mismatch is measured as 31 degree angle subtracted by 30 degree angle. The mismatch in orientation between what is seen and what is experienced will be 1 degree angle. This value is acceptable and below the threshold values.

At step 420, the method 400 includes identifying, by the virtual reality system, user experience of the user in the virtual reality motion simulator. If there is a mismatch between the visual perception measurement and the vestibular perception measurement of the virtual reality content, the user is likely to experience the virtual reality sickness. If there is a match between the visual perception measurement and the vestibular perception measurement of the virtual reality content, the user is likely to have a good experience of the virtual reality content.

FIG. 5 illustrates a block diagram of an exemplary computer system (or an electronic device) for implementing embodiments consistent with the present disclosure. Variations of computer system 501 may be used for performing optical character recognition on an image including a plurality of printed characters. The computer system 501 may comprise a central processing unit ("CPU" or "processor") 502. Processor 502 may comprise at least one data processor for executing program components for executing user- or system-generated requests. A user may include a person, a person using a device such as such as those included in this disclosure, or such a device itself. The processor may include specialized processing units such as integrated system (bus) controllers, memory management control units, floating point units, graphics processing units, digital signal processing units, etc. The processor may include a microprocessor, such as AMD Athlon, Duron or Opteron, ARM's application, embedded or secure processors, IBM PowerPC, Intel's Core, Itanium, Xeon, Celeron or other line of processors, etc. The processor 502 may be implemented using mainframe, distributed processor, multi-core, parallel, grid, or other architectures. Some embodiments may utilize embedded technologies like application-specific integrated circuits (ASICs), digital signal processors (DSPs), Field Programmable Gate Arrays (FPGAs), etc. In some embodiments, the processor 502 can include the comparison logic module 230 of FIG. 2 to compare the visual perception measurement and the vestibular perception measurement. In other embodiments, the comparison logic module 230 can be present external to the processor 502 and coupled to the processor 502.

Processor 502 may be disposed in communication with one or more input/output (I/O) devices via I/O interface 503. The I/O interface 503 may employ communication protocols/methods such as, without limitation, audio, analog, digital, monoaural, RCA, stereo, IEEE-1394, serial bus, universal serial bus (USB), infrared, PS/2, BNC, coaxial, component, composite, digital visual interface (DVI), high-definition multimedia interface (HDMI), RF antennas, S-Video, VGA, IEEE 802.n/b/g/n/x, Bluetooth, cellular (e.g., code-division multiple access (CDMA), high-speed packet access (HSPA+), global system for mobile communications (GSM), long-term evolution (LTE), WiMax, or the like), etc.

Using the I/O interface 503, the computer system 501 may communicate with one or more I/O devices. For example, the input device 504 may be an antenna, keyboard, mouse, joystick, (infrared) remote control, camera, card reader, fax machine, dongle, biometric reader, microphone, touch screen, touchpad, trackball, sensor (e.g., accelerometer, light sensor, GPS, gyroscope, proximity sensor, or the like), stylus, scanner, storage device, transceiver, video device/source, visors, etc. Output device 505 may be a printer, fax machine, video display (e.g., cathode ray tube (CRT), liquid crystal display (LCD), light-emitting diode (LED), plasma, or the like), audio speaker, etc. In some embodiments, a transceiver 506 may be disposed in connection with the processor 502. The transceiver may facilitate various types of wireless transmission or reception. For example, the transceiver may include an antenna operatively connected to a transceiver chip (e.g., Texas Instruments WiLink WL1283, Broadcom BCM4750IUB8, Infineon Technologies X-Gold 518-PMB9800, or the like), providing IEEE 802.11a/b/g/n, Bluetooth, FM, global positioning system (GPS), 2G/3G HSDPA/HSUPA communications, etc.

In some embodiments, the processor 502 may be disposed in communication with a communication network 508 via a network interface 507. The network interface 507 may communicate with the communication network 508. The network interface may employ connection protocols including, without limitation, direct connect, Ethernet (e.g., twisted pair 10/100/1000 Base T), transmission control protocol/internet protocol (TCP/IP), token ring, IEEE 802.11a/b/g/n/x, etc. The communication network 608 may include, without limitation, a direct interconnection, local area network (LAN), wide area network (WAN), wireless network (e.g., using Wireless Application Protocol), the Internet, etc. Using the network interface 507 and the communication network 508, the computer system 501 may communicate with devices 510, 511, and 512. These devices may include, without limitation, personal computer(s), server(s), fax machines, printers, scanners, various mobile devices such as cellular telephones, smartphones (e.g., Apple iPhone, Blackberry, Android-based phones, etc.), tablet computers, eBook readers (Amazon Kindle, Nook, etc.), laptop computers, notebooks, gaming consoles (Microsoft Xbox, Nintendo DS, Sony PlayStation, etc.), or the like. In some embodiments, the computer system 501 may itself embody one or more of these devices.

In some embodiments, the processor 502 may be disposed in communication with one or more memory devices (e.g., RAM 513, ROM 514, etc.) via a storage interface 512. The storage interface may connect to memory devices including, without limitation, memory drives, removable disc drives, etc., employing connection protocols such as serial advanced technology attachment (SATA), integrated drive electronics (IDE), IEEE-1394, universal serial bus (USB), fiber channel, small computer systems interface (SCSI), etc. The memory drives may further include a drum, magnetic disc drive, magneto-optical drive, optical drive, redundant array of independent discs (RAID), solid-state memory devices, solid-state drives, etc.

The memory devices may store a collection of program or database components, including, without limitation, an operating system 516, user interface application 517, web browser 518, mail server 519, mail client 520, user/application data 521 (e.g., any data variables or data records discussed in this disclosure), etc. The operating system 516 may facilitate resource management and operation of the computer system 501. Examples of operating systems include, without limitation, Apple Macintosh OS X, UNIX, Unix-like system distributions (e.g., Berkeley Software Distribution (BSD), FreeBSD, NetBSD, OpenBSD, etc.), Linux distributions (e.g., Red Hat, Ubuntu, Kubuntu, etc.), IBM OS/2, Microsoft Windows (XP, Vista/7/8, etc.), Apple iOS, Google Android, Blackberry OS, or the like. User interface 517 may facilitate display, execution, interaction, manipulation, or operation of program components through textual or graphical facilities. For example, user interfaces may provide computer interaction interface elements on a display system operatively connected to the computer system 501, such as cursors, icons, check boxes, menus, scrollers, windows, widgets, etc. Graphical user interfaces (GUIs) may be employed, including, without limitation, Apple Macintosh operating systems' Aqua, IBM OS/2, Microsoft Windows (e.g., Aero, Metro, etc.), Unix X-Windows, web interface libraries (e.g., ActiveX, Java, Javascript, AJAX, HTML, Adobe Flash, etc.), or the like.

In some embodiments, the computer system 501 may implement a web browser 518 stored program component. The web browser may be a hypertext viewing application, such as Microsoft Internet Explorer, Google Chrome, Mozilla Firefox, Apple Safari, etc. Secure web browsing may be provided using HTTPS (secure hypertext transport protocol), secure sockets layer (SSL), Transport Layer Security (TLS), etc. Web browsers may utilize facilities such as AJAX, DHTML, Adobe Flash, JavaScript, Java, application programming interfaces (APIs), etc. In some embodiments, the computer system 501 may implement a mail server 519 stored program component. The mail server 519 may be an Internet mail server such as Microsoft Exchange, or the like. The mail server 519 may utilize facilities such as ASP, ActiveX, ANSI C++/C#, Microsoft .NET, CGI scripts, Java, JavaScript, PERL, PHP, Python, WebObjects, etc. The mail server 519 may utilize communication protocols such as internet message access protocol (IMAP), messaging application programming interface (MAPI), Microsoft Exchange, post office protocol (POP), simple mail transfer protocol (SMTP), or the like. In some embodiments, the computer system 501 may implement a mail client 520 stored program component. The mail client may be a mail viewing application, such as Apple Mail, Microsoft Entourage, Microsoft Outlook, Mozilla Thunderbird, etc.

In some embodiments, computer system 501 may store user/application data 521, such as the data, variables, records, etc. as described in this disclosure. Such databases may be implemented as fault-tolerant, relational, scalable, secure databases such as Oracle or Sybase. Alternatively, such databases may be implemented using standardized data structures, such as an array, hash, linked list, struct, structured text file (e.g., XML), table, or as object-oriented databases (e.g., using ObjectStore, Poet, Zope, etc.). Such databases may be consolidated or distributed, sometimes among the various computer systems discussed above in this disclosure. It is to be understood that the structure and operation of the any computer or database component may be combined, consolidated, or distributed in any working combination.

Furthermore, one or more computer-readable storage media may be utilized in implementing embodiments consistent with this technology. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term "computer-readable medium" should be understood to include tangible items and exclude carrier waves and transient signals, i.e., non-transitory. Examples include Random Access Memory (RAM), Read-Only Memory (ROM), volatile memory, nonvolatile memory, hard drives, Compact Disc (CD) ROMs, Digital Video Disc (DVDs), flash drives, disks, and any other known physical storage media.

Embodiments of the present disclosure provide a method and system for detecting virtual reality sickness causing content in virtual reality motion simulators. The present disclosure detects and prevents virtual reality sickness among end users of a virtual reality content. The present disclosure solves virtual reality sickness in virtual reality motion simulators where physical motion is also simulated in addition to simulation through head mounted virtual reality device. The present disclosure certifies that a combination of virtual reality application and the virtual reality motion simulator will not cause virtual reality sickness and disorientation in the user. The present disclosure is used to identify and report which sections of the virtual reality content developed for virtual reality motion simulators will cause virtual reality sickness. Application developers are hence enabled to remove sickness-causing content during development of the virtual reality application itself. The present disclosure is also used to sense biological parameters of the user including electrocardiogram, blood pressure, biological anxiety parameters and co-relate it with orientation mismatch between visual and vestibular systems.

The terms "an embodiment", "embodiment", "embodiments", "the embodiment", "the embodiments", "one or more embodiments", "some embodiments", and "one embodiment" mean "one or more (but not all) embodiments of the invention(s)" unless expressly specified otherwise.

The terms "including", "comprising", "having" and variations thereof mean "including but not limited to", unless expressly specified otherwise.

The enumerated listing of items does not imply that any or all of the items are mutually exclusive, unless expressly specified otherwise.

The terms "a", "an" and "the" mean "one or more", unless expressly specified otherwise.

A description of an embodiment with several components in communication with each other does not imply that all such components are required. On the contrary a variety of optional components are described to illustrate the wide variety of possible embodiments of this technology.

When a single device or article is described herein, it will be readily apparent that more than one device/article (whether or not they cooperate) may be used in place of a single device/article. Similarly, where more than one device or article is described herein (whether or not they cooperate), it will be readily apparent that a single device/article may be used in place of the more than one device or article or a different number of devices/articles may be used instead of the shown number of devices or programs. The functionality and/or the features of a device may be alternatively embodied by one or more other devices which are not explicitly described as having such functionality/features. Thus, other embodiments of this technology need not include the device itself.

The illustrated operations of FIG. 5 show certain events occurring in a certain order. In alternative embodiments, certain operations may be performed in a different order, modified or removed. Moreover, steps may be added to the above described logic and still conform to the described embodiments. Further, operations described herein may occur sequentially or certain operations may be processed in parallel. Yet further, operations may be performed by a single processing unit or by distributed processing units.

Finally, the language used in the specification has been principally selected for readability and instructional purposes, and it may not have been selected to delineate or circumscribe the inventive subject matter. It is therefore intended that the scope of the invention be limited not by this detailed description, but rather by any claims that issue on an application based here on. Accordingly, the disclosure of the embodiments of this technology is intended to be illustrative, but not limiting, of the scope of the invention, which is set forth in the following claims.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A method of detecting virtual reality sickness-causing content in virtual reality motion simulators, the method comprising:
   determining, by a virtual reality computing device, a visual perception measurement of a virtual reality content being displayed on a head-mounted virtual reality device of a virtual reality motion simulator;
   determining, by the virtual reality computing device, a vestibular perception measurement of the virtual reality content based on a first sensor data associated with a physical orientation of a platform of the virtual reality simulator and a second sensor data associated with a physical orientation of a head of a user;
   comparing, by the virtual reality computing device, the visual perception measurement and the vestibular perception measurement of the virtual reality content;
   determining, by the virtual reality computing device, an indication of a user experience in the virtual reality motion simulator based on the comparison; and
   outputting, by the virtual reality computing device, the indication of the user experience.

2. The method as claimed in claim 1, further comprising determining, by the virtual reality computing device, a visual orientation angle of the virtual reality content based on a relative angle of a virtual floor with respect to a virtual camera.

3. The method as claimed in claim 1, further comprising:
   measuring, by the virtual reality computing device, the first sensor data from a platform inertial measurement unit (IMU) sensor attached to the platform of the virtual reality motion simulator;
   measuring, by the virtual reality computing device, the second sensor data from at least one head mounted IMU sensor attached to the head mounted virtual reality device;
   combining, by the virtual reality computing device, the first sensor data and the second sensor data to derive orientation values; and
   determining, by the virtual reality computing device, a vestibular perception angle based on the orientation values.

4. The method as claimed in claim 1, wherein the virtual reality content is sensed by the user mounted on the platform of the virtual reality motion simulator and wearing the head-mounted virtual reality device and the method further comprises determining, by the virtual reality computing device, the virtual reality content as a virtual reality sickness-causing content based on a mismatch between the visual perception measurement and the vestibular perception measurement of the virtual reality content.

5. The method as claimed in claim 4, further comprising providing, by the virtual reality computing device, at least one correction method to correct the mismatch between the visual perception measurement and the vestibular perception measurement of the virtual reality content.

6. The method as claimed in claim 1, further comprising determining, by the virtual reality computing device, the virtual reality content as safe content based on a match between the visual perception measurement and the vestibular perception measurement of the virtual reality content.

7. A virtual reality computing device, comprising a processor and a memory communicatively coupled to the processor, wherein the memory comprises processor-executable instructions stored thereon, which when executed by the processor, cause the processor to:
   determine a visual perception measurement of a virtual reality content being displayed on a head-mounted virtual reality device of a virtual reality motion simulator;
   determine a vestibular perception measurement of the virtual reality content based on a first sensor data associated with a physical orientation of a platform of the virtual reality simulator and a second sensor data associated with a physical orientation of a head of a user;
   compare the visual perception measurement and the vestibular perception measurement of the virtual reality content;
   determine an indication of a user experience in the virtual reality motion simulator based on the comparison; and
   output the indication of the user experience.

8. The virtual reality computing device as claimed in claim 7, wherein the processor-executable instructions, when executed by the processor, further cause the processor to determine a visual orientation angle of the virtual reality content based on a relative angle of a virtual floor with respect to a virtual camera.

9. The virtual reality computing device as claimed in claim 7, wherein the processor-executable instructions, when executed by the processor, further cause the processor to:
measure the first sensor data from a platform inertial measurement unit (IMU) sensor attached to the platform of the virtual reality motion simulator;
measure the second sensor data from at least one head mounted IMU sensor attached to the head mounted virtual reality device;
combine the first sensor data and the second sensor data to derive orientation values; and
determine a vestibular perception angle based on the orientation values.

10. The virtual reality computing device as claimed in claim 7, wherein the virtual reality content is sensed by the user mounted on the platform of the virtual reality motion simulator and wearing the head-mounted virtual reality device and the processor-executable instructions, when executed by the processor, further cause the processor to determine the virtual reality content as a virtual reality sickness-causing content based on a mismatch between the visual perception measurement and the vestibular perception measurement of the virtual reality content.

11. The virtual reality computing device as claimed in claim 10, wherein the processor-executable instructions, when executed by the processor, further cause the processor to provide at least one correction method to correct the mismatch between the visual perception measurement and the vestibular perception measurement of the virtual reality content.

12. The virtual reality computing device as claimed in claim 11, wherein the processor-executable instructions, when executed by the processor, further cause the processor to determine the virtual reality content as safe content based on a match between the visual perception measurement and the vestibular perception measurement of the virtual reality content.

13. A non-transitory computer readable medium having stored thereon instructions for detecting virtual reality sickness-causing content in virtual reality motion simulators comprising executable code which when executed by one or more processors, causes the one or more processors to:
determine a visual perception measurement of a virtual reality content being displayed on a head-mounted virtual reality device of a virtual reality motion simulator;
determine a vestibular perception measurement of the virtual reality based on a first sensor data associated with a physical orientation of a platform of the virtual reality simulator and a second sensor data associated with a physical orientation of a head of a user;
compare the visual perception measurement and the vestibular perception measurement of the virtual reality content;
determine an indication of a user experience in the virtual reality motion simulator based on the comparison; and
output the indication of the user experience.

14. The non-transitory computer readable medium as claimed in claim 13, wherein the executable code when executed by the one or more processors further causes the one or more processors to determine a visual orientation angle of the virtual reality content based on a relative angle of a virtual floor with respect to a virtual camera.

15. The non-transitory computer readable medium as claimed in claim 13, wherein the executable code when executed by the one or more processors further causes the one or more processors to:
measure the first sensor data from a platform inertial measurement unit (IMU) sensor attached to the platform of the virtual reality motion simulator;
measure the second sensor data from at least one head mounted IMU sensor attached to the head mounted virtual reality device;
combine the first sensor data and the second sensor data to derive orientation values; and
determine a vestibular perception angle based on the orientation values.

16. The non-transitory computer readable medium as claimed in claim 13, wherein the virtual reality content is sensed by the user mounted on the platform of the virtual reality motion simulator and wearing the head-mounted virtual reality device and the executable code when executed by the one or more processors further causes the one or more processors to determine the virtual reality content as a virtual reality sickness-causing content based on a mismatch between the visual perception measurement and the vestibular perception measurement of the virtual reality content.

17. The non-transitory computer readable medium as claimed in claim 16, wherein the executable code when executed by the one or more processors further causes the one or more processors to provide at least one correction method to correct the mismatch between the visual perception measurement and the vestibular perception measurement of the virtual reality content.

18. The non-transitory computer readable medium as claimed in claim 13, wherein the executable code when executed by the one or more processors further causes the one or more processors to determine the virtual reality content as safe content based on a match between the visual perception measurement and the vestibular perception measurement of the virtual reality content.

* * * * *